(12) United States Patent
Santos

(10) Patent No.: US 11,020,318 B2
(45) Date of Patent: Jun. 1, 2021

(54) PUSH RELEASE CLOSED SYSTEM DRUG TRANSFER APPARATUS

(71) Applicant: John Santos, Pinole, CA (US)

(72) Inventor: John Santos, Pinole, CA (US)

(*) Notice: Subject to any disclaimer, the term of this patent is extended or adjusted under 35 U.S.C. 154(b) by 221 days.

(21) Appl. No.: 16/253,679

(22) Filed: Jan. 22, 2019

(65) Prior Publication Data

US 2020/0230026 A1 Jul. 23, 2020

(51) Int. Cl.
*A61J 1/20* (2006.01)
*A61M 5/32* (2006.01)
*A61M 5/178* (2006.01)

(52) U.S. Cl.
CPC .......... *A61J 1/2048* (2015.05); *A61J 1/2096* (2013.01); *A61M 5/1782* (2013.01); *A61M 5/32* (2013.01)

(58) Field of Classification Search
CPC .............. A61J 1/20–2096; A61J 1/2048; A61J 1/2096; A61M 5/1782; A61M 5/32; A61M 39/1011
USPC ......................................................... 604/414
See application file for complete search history.

(56) References Cited

U.S. PATENT DOCUMENTS

| | | | |
|---|---|---|---|
| 2,627,857 A * | 2/1953 | Marcelli | A61M 5/1782 604/407 |
| 3,605,744 A * | 9/1971 | Dwyer | A61M 5/2033 604/506 |
| 4,141,461 A | 2/1979 | LaChance | |
| 4,144,461 A | 3/1979 | Glasser | |
| 4,258,713 A * | 3/1981 | Wardlaw | A61M 5/2033 604/139 |
| 4,673,813 A | 6/1987 | Sanchez | |
| 7,648,491 B2 * | 1/2010 | Rogers | A61M 39/26 604/414 |
| 8,106,372 B2 | 1/2012 | Powers | |
| 8,110,821 B2 | 2/2012 | Lemer | |
| 8,348,903 B2 | 1/2013 | Baplue | |
| 8,633,461 B2 | 1/2014 | Fago | |
| D778,460 S | 2/2017 | Marechal | |
| 10,744,315 B2 * | 8/2020 | Sanders | A61J 1/1406 |

FOREIGN PATENT DOCUMENTS

WO WO2007016171 2/2007

* cited by examiner

*Primary Examiner* — Nicholas J Weiss
*Assistant Examiner* — Seth Han

(57) ABSTRACT

A push release closed system drug transfer apparatus for easy and secure drug transfer includes a cylindrical housing having a cylindrical housing having a top end, an outer wall, and a bottom end forming an inner cavity. The top end has a syringe aperture to receive a syringe. A needle tube is coupled to the cylindrical housing and extends from the syringe aperture to a principal aperture to receive a needle of the syringe. An inner cylinder is configured to selectively engage connector of a vial. An ejector spring moves the inner cylinder from a compressed position to an alternate decompressed position. A lock mechanism and a release secure the inner cylinder in the compressed position and alternatively free the inner cylinder to move to the alternate decompressed position.

10 Claims, 4 Drawing Sheets

PUSH RELEASE CLOSED SYSTEM DRUG TRANSFER APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to closed system drug transfers and more particularly pertains to a new closed system drug transfer for easy and secure drug transfer.

BRIEF SUMMARY OF THE INVENTION

An embodiment of the disclosure meets the needs presented above by generally comprising a cylindrical housing having a top end, an outer wall, and a bottom end forming an inner cavity. The top end has a syringe aperture extending through to the inner cavity. The syringe aperture is configured to receive a syringe. The bottom end has a principal aperture extending through to the inner cavity. A needle tube is coupled to the cylindrical housing and extends from the syringe aperture to the principal aperture within the inner cavity. The needle tube is configured to receive a needle of the syringe. An inner cylinder is slidably coupled within the principal aperture. The inner cylinder has a shaft having a top side and a bottom side and a nipple coupled to the bottom side. The inner cylinder has a compressed position with the shaft within the inner cavity of the cylindrical housing and the nipple extending through the principal aperture. The inner cylinder has an alternate decompressed position with the shaft extended through the principal aperture. The nipple is configured to selectively engage a connector of a vial. The inner cylinder has a central aperture extending from the top side of the shaft through the nipple to receive the needle tube. An ejector spring is coupled to the cylindrical housing and the inner cylinder to move the inner cylinder from the compressed position to the alternate decompressed position. A lock mechanism is coupled to the top side of the inner cylinder. A release is coupled to the cylindrical housing through the outer wall and in operational communication with the lock mechanism. The release secures the inner cylinder in the compressed position and alternatively frees the inner cylinder to move to the alternate decompressed position.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
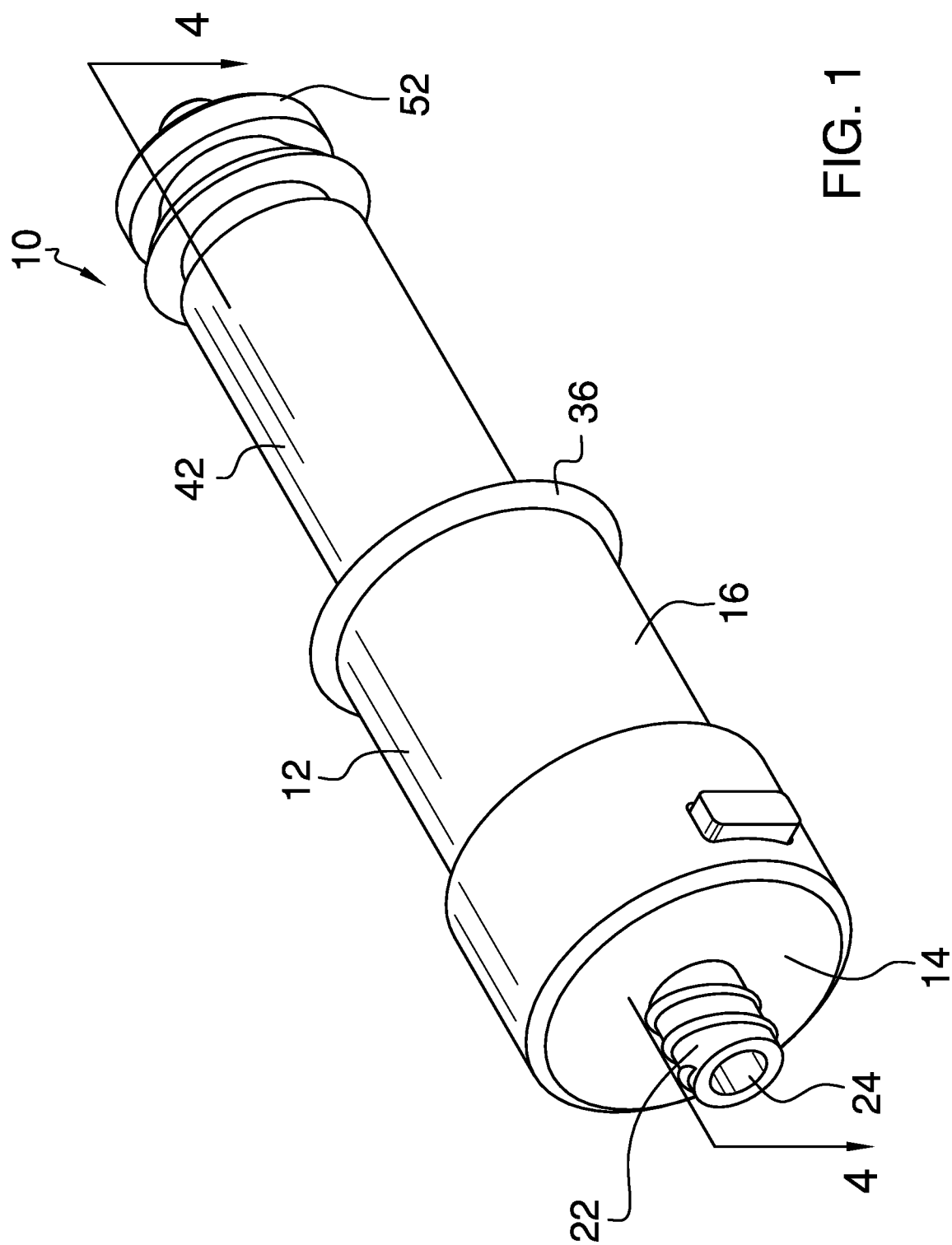
FIG. 1 is an isometric view of a push release closed system drug transfer apparatus according to an embodiment of the disclosure.
Figure 2:
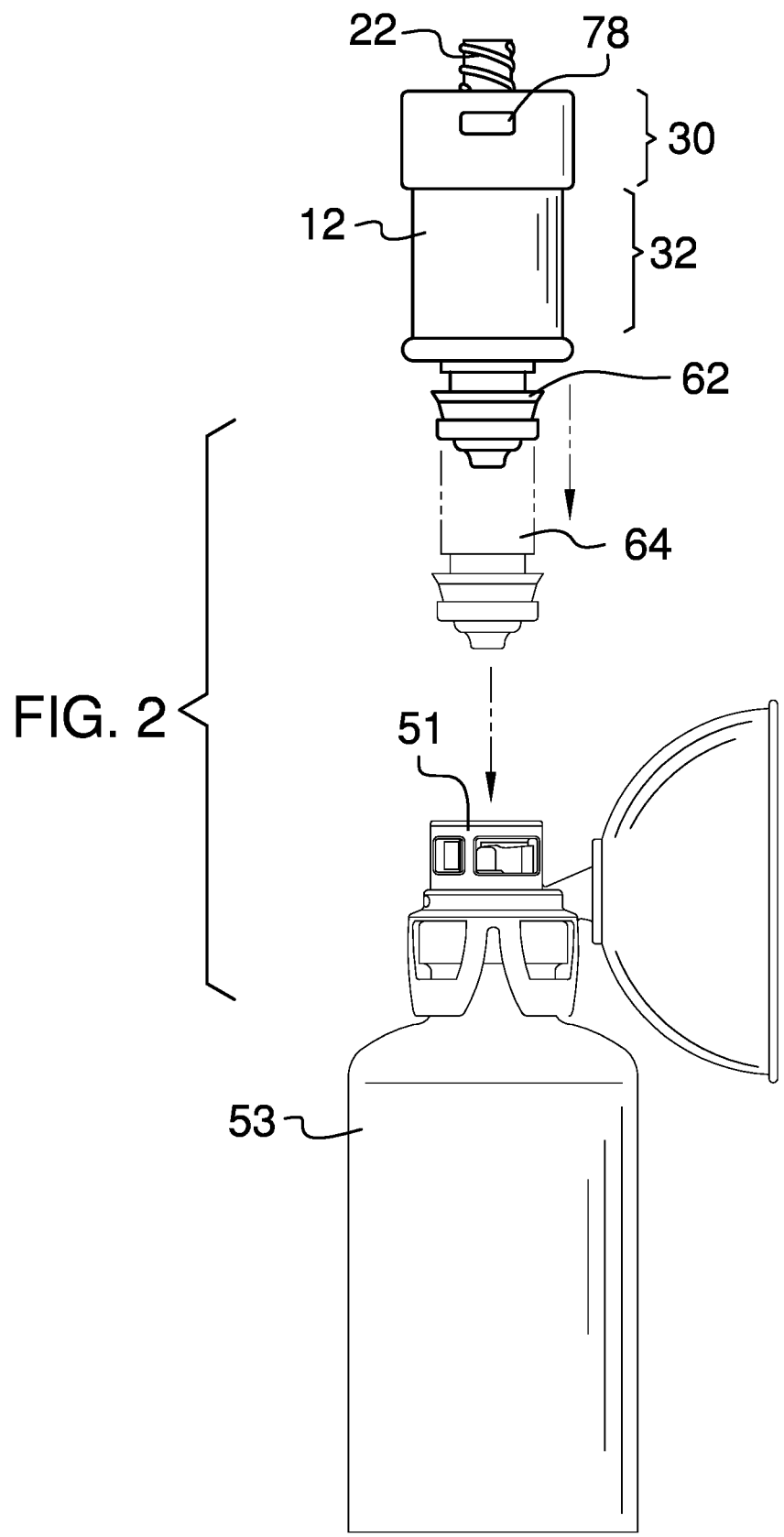
FIG. 2 is a side elevation view of an embodiment of the disclosure.
Figure 3:
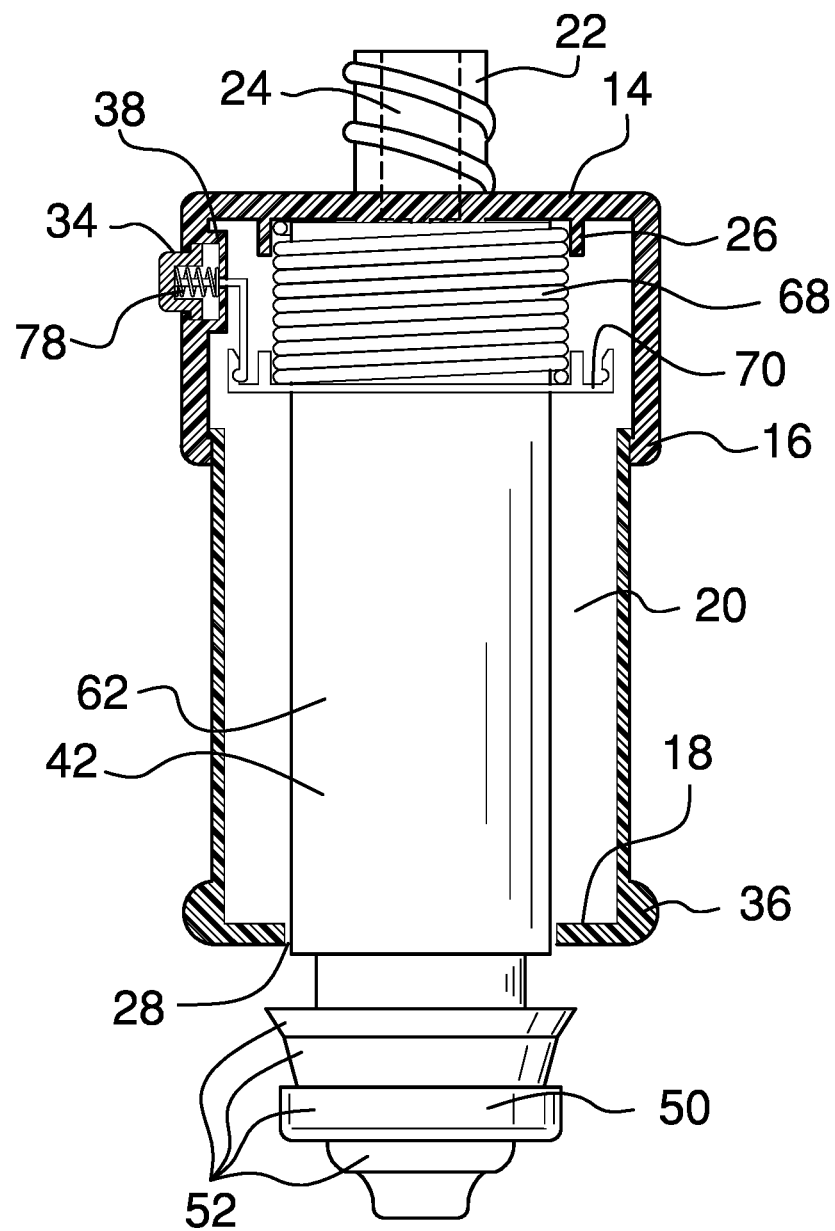
FIG. 3 is a cross-sectional view of an embodiment of the disclosure.
Figure 4:
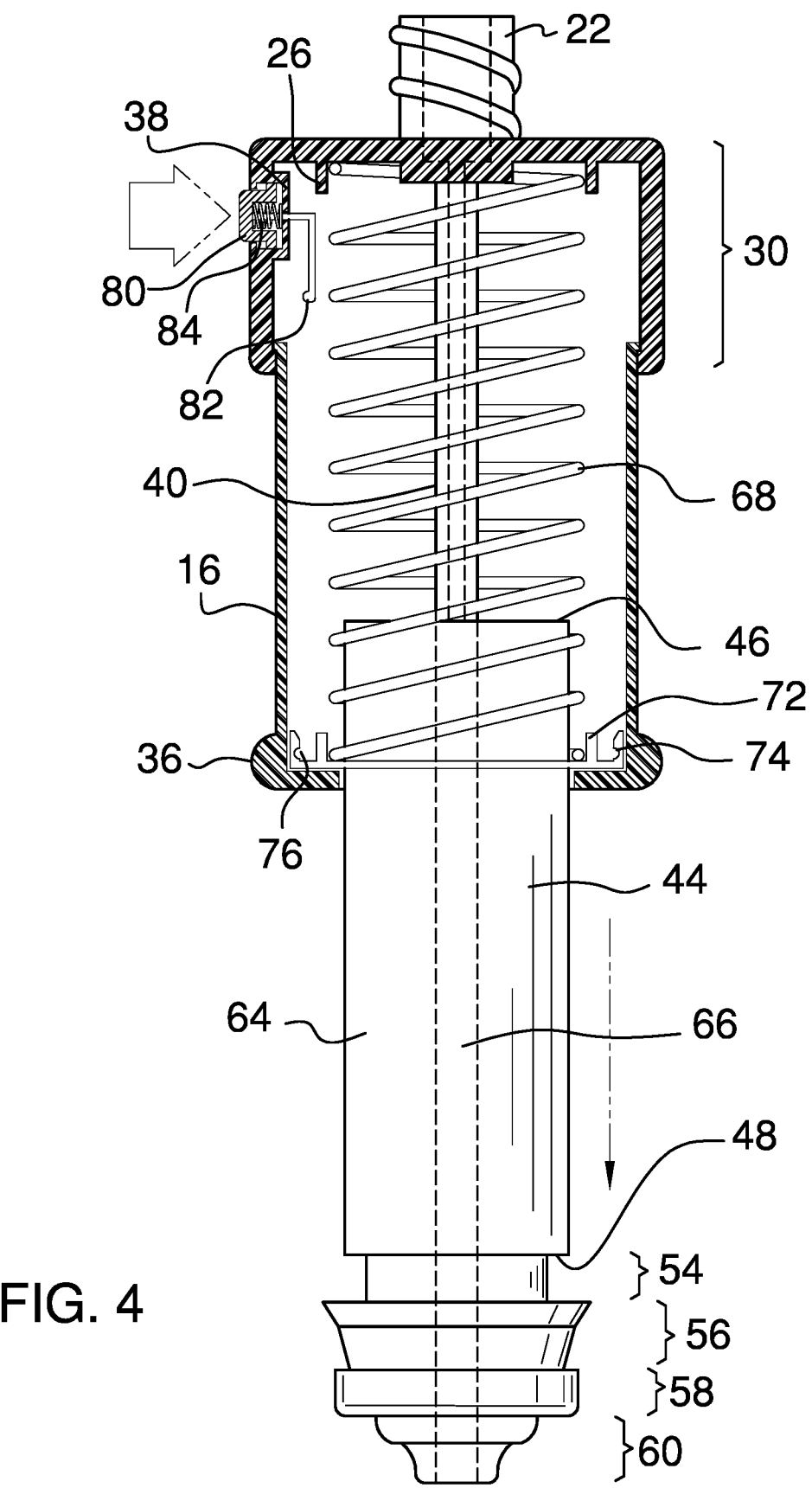
FIG. 4 is a cross-sectional view of an embodiment of the disclosure along line 4-4 of FIG. 1.

With reference now to the drawings, and in particular to FIGS. 1 through 4 thereof, a new closed system drug transfer embodying the principles and concepts of an embodiment of the disclosure and generally designated by the reference numeral 10 will be described.

As best illustrated in FIGS. 1 through 4, the push release closed system drug transfer apparatus 10 generally comprises a cylindrical housing 12 having a top end 14, an outer wall 16, and a bottom end 18 forming an inner cavity 20. The top end 14 has a syringe extension 22 extending away from the inner cavity 20 and a syringe aperture 24 extending through the syringe extension 22 to the inner cavity 20. The syringe extension 22 may be threaded. The syringe aperture 24 is configured to receive a syringe. A spring stop 26 may be coupled to the top end 14 within the inner cavity 20 and concentric with the syringe aperture 24. The bottom end 18 has a principal aperture 28 extending through to the inner cavity 20. The outer wall 16 has an upper portion 30 and a lower portion 32. The upper portion 30 is wider than the lower portion 32. The upper portion 30 has a button aperture 34 extending through to the inner cavity 20 and the lower portion 32 has a lip 36 adjacent the bottom end 18. A button housing 38 is coupled to the outer wall 16 within the inner cavity 20 adjacent the button aperture 34. A needle tube 40 is coupled to the cylindrical housing 12 and extends from the syringe aperture 24 to the principal aperture 28 within the inner cavity. The needle tube 40 is configured to receive a needle of the syringe.

An inner cylinder 42 is slidably coupled within the principal aperture 28. The inner cylinder 42 has a shaft 44 having a top side 46 and a bottom side 48 and a nipple 50 coupled to the bottom side 48. The nipple 50 may comprise a plurality of tiers 52 comprising a straight portion 54, a curved portion 56, a flange portion 58, and a tip 60. The inner cylinder 42 has a compressed position 62 with the shaft 44 within the inner cavity 20 of the cylindrical housing and the nipple 50 extending through the principal aperture 28. The inner cylinder 42 has an alternate decompressed position 64 with the shaft 44 extended through the principal aperture 28. The nipple 50 is configured to selectively engage a connector 51 of a vial 53. The inner cylinder 42 has a central aperture 66 extending from the top side 46 of the shaft through the nipple 50 to receive the needle tube 40 when in the compressed position 62.

An ejector spring 68 is coupled to the cylindrical housing 12 and the inner cylinder 42. The ejector spring 68 is coupled within the spring stop 26 of the cylindrical housing. The ejector spring 68 moves the inner cylinder 42 from the compressed position 62 to the alternate decompressed position 64. A lock mechanism 70 is coupled to the top side 46 of the inner cylinder 42. The lock mechanism 70 comprises an inner ring 72 and an outer ring 74. The inner ring 72 is coupled to the ejector spring 68 and the outer ring has a catch 76. A release 78 is within the button housing 38 through the outer wall 16 and in operational communication with the lock mechanism 70. The release 78 may comprise a button 80, a hook 82, and a button spring 84. The hook 82 is coupled to the button 80 and extends through the button housing 38 to selectively engage the catch 76 and secure the inner cylinder 42 in the compressed position 62. The button spring 84 is coupled between the button 80 and the button housing 38 around the hook 82. The button 80 is depressible to move the hook 82 off the catch to allow the inner cylinder 42 to move to the alternate decompressed position 64.

In use, the nipple 50 is engaged with the connector of the vial and the syringe is inserted through the syringe aperture 24 to draw medicine. When complete, the button 80 is depressed to move the inner cylinder 42 to the alternate decompressed position 64 to safely withdraw the syringe from the vial.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A push release closed system drug transfer apparatus comprising:
    a cylindrical housing, the cylindrical housing having a top end, an outer wall, and a bottom end forming an inner cavity, the outer wall having a button aperture extending through to the inner cavity, the top end having a syringe aperture extending through to the inner cavity, the syringe aperture being configured to receive a syringe, the bottom end having a principal aperture extending through to the inner cavity;
    a needle tube coupled to the cylindrical housing, the needle tube extending from the syringe aperture to the principal aperture within the inner cavity, the needle tube being configured to receive a needle of the syringe;
    an inner cylinder coupled to the cylindrical housing, the inner cylinder being slidably coupled within the principal aperture, the inner cylinder having a shaft having a top side and a bottom side and a nipple coupled to the bottom side, the inner cylinder having a compressed position with the shaft within the inner cavity of the cylindrical housing and the nipple extending through the principal aperture, the inner cylinder having an alternate decompressed position with the shaft extended through the principal aperture, the nipple being configured to selectively engage a connector of a vial, the inner cylinder having a central aperture extending from the top side of the shaft through the nipple, the central aperture receiving the needle tube;
    an ejector spring coupled to the cylindrical housing and the inner cylinder, the ejector spring moving the inner cylinder from the compressed position to the alternate decompressed position;
    a lock mechanism coupled to the inner cylinder, the lock mechanism being coupled to the top side, the lock mechanism comprising an inner ring and an outer ring, the inner ring and the outer ring being concentrically positioned wherein the inner ring is positioned within an interior space of the outer ring defined by a perimeter of the outer ring, the inner ring being coupled to the ejector spring, the outer ring having a catch;
    a release coupled to the cylindrical housing, the release being coupled through the outer wall and in operational communication with the lock mechanism, the release securing the inner cylinder in the compressed position and alternatively freeing the inner cylinder to move to the alternate decompressed position; and
    a button housing being coupled to the outer wall within the inner cavity adjacent the button aperture, the release being coupled within the button housing.

2. The push release closed system drug transfer apparatus of claim 1 further comprising the cylindrical housing having a syringe extension extending from the top end, the syringe aperture extending through the syringe extension.

3. The push release closed system drug transfer apparatus of claim 2 further comprising the syringe extension being threaded.

4. The push release closed system drug transfer apparatus of claim 1 further comprising the outer wall of the cylindrical housing having an upper portion and a lower portion, the upper portion being wider than the lower portion.

5. The push release closed system drug transfer apparatus of claim 4 further comprising the lower portion having a lip, the lip being adjacent the bottom end.

6. The push release closed system drug transfer apparatus of claim 1 further comprising the nipple comprising a plurality of tiers.

7. The push release closed system drug transfer apparatus of claim 6 further comprising the plurality of tiers further comprising a straight portion, a curved portion, a flange portion, and a tip.

8. The push release closed system drug transfer apparatus of claim 1 further comprising the cylindrical housing having a spring stop coupled to the top end within the inner cavity, the spring stop being concentric with the syringe aperture.

9. The push release closed system drug transfer apparatus of claim 1 further comprising the release comprising a button, a hook, and a button spring, the hook being coupled to the button and extending through the button housing to selectively engage the catch, the button spring being coupled between the button and the button housing around the hook, the button being depressible to move the hook off the catch to allow the inner cylinder to move to the alternate decompressed position.

10. A push release closed system drug transfer apparatus comprising:
- a cylindrical housing, the cylindrical housing having a top end, an outer wall, and a bottom end forming an inner cavity, the top end having a syringe extension extending away from the inner cavity and a syringe aperture extending through the syringe extension to the inner cavity, the syringe extension being threaded, the syringe aperture being configured to receive a syringe, a spring stop being coupled to the top end within the inner cavity and concentric with the syringe aperture, the bottom end having a principal aperture extending through to the inner cavity, the outer wall having an upper portion and a lower portion, the upper portion being wider than the lower portion, the upper portion having a button aperture extending through to the inner cavity, the lower portion having a lip adjacent the bottom end;
- a button housing coupled to the cylindrical housing, the button housing being coupled to the outer wall within the inner cavity adjacent the button aperture;
- a needle tube coupled to the cylindrical housing, the needle tube extending from the syringe aperture to the principal aperture within the inner cavity, the needle tube being configured to receive a needle of the syringe;
- an inner cylinder coupled to the cylindrical housing, the inner cylinder being slidably coupled within the principal aperture, the inner cylinder having a shaft having a top side and a bottom side and a nipple coupled to the bottom side, the nipple comprising a plurality of tiers comprising a straight portion, a curved portion, a flange portion, and a tip, the inner cylinder having a compressed position with the shaft within the inner cavity of the cylindrical housing and the nipple extending through the principal aperture, the inner cylinder having an alternate decompressed position with the shaft extended through the principal aperture, the nipple being configured to selectively engage a connector of a vial, the inner cylinder having a central aperture extending from the top side of the shaft through the nipple, the central aperture receiving the needle tube;
- an ejector spring coupled to the cylindrical housing and the inner cylinder, the ejector spring being coupled within the spring stop of the cylindrical housing, the ejector spring moving the inner cylinder from the compressed position to the alternate decompressed position;
- a lock mechanism coupled to the inner cylinder, the lock mechanism being coupled to the top side, the lock mechanism comprising an inner ring and an outer ring, the inner ring and the outer ring being concentrically positioned wherein the inner ring is positioned within an interior space of the outer ring defined by a perimeter of the outer ring, the inner ring being coupled to the ejector spring, the outer ring having a catch; and
- a release coupled to the cylindrical housing, the release being coupled within the button housing through the outer wall and in operational communication with the lock mechanism, the release comprising a button, a hook, and a button spring, the hook being coupled to the button and extending through the button housing to selectively engage the catch and secure the inner cylinder in the compressed position, the button spring being coupled between the button and the button housing around the hook, the button being depressible to move the hook off the catch to allow the inner cylinder to move to the alternate decompressed position.

* * * * *